(12) United States Patent
Jin et al.

(10) Patent No.: US 12,207,886 B2
(45) Date of Patent: Jan. 28, 2025

(54) SURGERY TOOL SEGMENTATION WITH ROBOT KINEMATICS

(71) Applicant: Verily Life Sciences LLC, South San Francisco, CA (US)

(72) Inventors: Xing Jin, San Jose, CA (US); Joëlle Barral, Mountain View, CA (US); Martin Habbecke, Palo Alto, CA (US); Caitlin Donhowe, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1131 days.

(21) Appl. No.: 16/947,240

(22) Filed: Jul. 24, 2020

(65) Prior Publication Data
US 2021/0030483 A1 Feb. 4, 2021

Related U.S. Application Data

(60) Provisional application No. 62/879,677, filed on Jul. 29, 2019.

(51) Int. Cl.
A61B 34/20 (2016.01)
A61B 34/30 (2016.01)
B25J 17/02 (2006.01)
G06T 7/143 (2017.01)
G06V 10/25 (2022.01)

(52) U.S. Cl.
CPC .............. A61B 34/20 (2016.02); A61B 34/30 (2016.02); B25J 17/0283 (2013.01); G06T 7/143 (2017.01); G06V 10/25 (2022.01); A61B 2034/2059 (2016.02); A61B 2034/2065 (2016.02); A61B 2034/301 (2016.02); G06T 2207/20084 (2013.01); G06T 2207/20112 (2013.01)

(58) Field of Classification Search
CPC . A61B 34/20; A61B 34/30; A61B 2034/2059; A61B 2034/2065; A61B 2034/301; G06T 7/143; G06T 2207/20084; G06T 2207/20112; G06V 10/25; B25J 17/0283; B25J 17/00; B25J 18/00
See application file for complete search history.

(56) References Cited

U.S. PATENT DOCUMENTS

2009/0088897 A1* 4/2009 Zhao ...................... A61B 34/37
700/250
2009/0192524 A1* 7/2009 Itkowitz ............... A61B 90/361
606/130

(Continued)

Primary Examiner — Edward F Urban
Assistant Examiner — Duy Tran
(74) Attorney, Agent, or Firm — Kilpatrick Townsend & Stockton LLP

(57) ABSTRACT

Systems and methods for identifying surgery tools of a robotic surgery system in surgery video based on robot kinematics are described. Kinematic data describing a position of a first robotic surgery arm including a surgery tool is used to determine a nominal position of the first robotic surgery arm. A search area within image data obtained during a robotic surgery from an endoscope attached to a second robotic surgery arm is determined based on the kinematic data and a nominal position of the surgery tool. The surgery tool is identified within the search area of the image data using an object detection technique.

20 Claims, 12 Drawing Sheets

(56) References Cited

U.S. PATENT DOCUMENTS

2015/0297313 A1* 10/2015 Reiter .................. A61B 5/7267
 600/408
2017/0143429 A1* 5/2017 Richmond ............. A61B 34/37
2017/0189131 A1* 7/2017 Weir ...................... B25J 9/1689
2017/0354470 A1* 12/2017 Farritor .............. A61B 18/1482

* cited by examiner

SURGERY TOOL SEGMENTATION WITH ROBOT KINEMATICS

CROSS-REFERENCE TO RELATED APPLICATIONS

This application claims priority to U.S. Provisional Patent Application No. 62/879,677, filed Jul. 29, 2019, titled "Surgery Tool Segmentation With Robot Kinematics," the entirety of which is hereby incorporated by reference.

BACKGROUND

In recent years, robotic surgeries have become increasingly popular because of their advantages over the traditional human-operated open surgeries. Surgical tools used in robotic surgeries have improved levels of dexterity over a human surgeon. These tools can provide the surgeon maximum range of motion and precision. In addition, high-definition cameras associated with the surgical tools can provide a better view of the operating site to the surgeon than are otherwise typically available. Further, the small size of the robotic surgical tools allows the surgeries to be done in a minimally invasive manner thereby causing less trauma to the patient's body.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method, including: receiving image data from a camera disposed at a first distal end of a first robotic surgery arm, the image data at least representing a second distal end of a second robotic surgery arm, receiving system property data providing dimensions of the second robotic surgery arm, and receiving kinematic pose data providing a plurality of joint angles of the second robotic surgery arm. The computer-implemented method further includes determining, based at least in part on the kinematic pose data and the system property data, a nominal position of the second robotic surgery arm relative to a position of the camera. The computer-implemented method further includes determining a search area including a subset of the image data representing the second robotic surgery arm based on the nominal position and identifying, using an object detection technique and based on the subset of the image data, the second distal end of the second robotic surgery arm within the image data. Other embodiments of this aspect include corresponding computer systems, apparatus, and computer programs recorded on one or more computer storage devices, each configured to perform the actions of the methods.

Another example includes one or more non-transitory computer-readable media having computer-executable instructions that, when executed by one or more computing systems, cause the one or more computing systems to: receive first image data from a camera disposed at a first distal end of a first robotic surgery arm at a first time, the first image data at least representing a second distal end of a second robotic surgery arm. The instructions further cause the computer systems to receive system property data providing dimensions of the second robotic surgery arm and receiving first kinematic pose data providing a plurality of joint angles of the second robotic surgery arm. The instructions further cause the computer systems to determine an expected position of the second robotic surgery arm within the first image data based on the first kinematic pose data and the system property data and determine a first search area including a subset of the first image data representing the expected position of the second robotic surgery arm. The instructions further cause the computer systems to identify, using an object recognition technique within the first search area, an actual position of the second distal end of the second robotic surgery arm within the first image data. After identifying the actual position, the instructions cause the computer systems to determine an offset value based on comparing the nominal position and the actual position of the second distal end of the second robotic surgery arm. The computer systems then receive second image data from the camera at a second time along with second kinematic pose data providing the plurality of joint angles of the second robotic surgery arm at the second time. Based on the offset value and the second kinematic data, the instructions cause the computer systems to determine a second search area including a subset of the second image data representing an anticipated position of the second robotic surgery arm based on the offset value and the second kinematic pose data. The instructions further cause the computer systems to identify, using the object recognition technique within the second search area, the second robotic surgery arm within the second image data.

One general aspect includes a computer-implemented method, including: receiving image data from a camera disposed at a first distal end of a first robotic surgery arm, receiving system property data providing dimensions of a second robotic surgery arm and describing compliance of the second robotic surgery arm, and receiving kinematic pose data providing a plurality of joint angles of the second robotic surgery arm. The computer-implemented method includes determining, based on the system property data and the kinematic pose data, a nominal position of the second robotic surgery arm within the image data. The computer-implemented method then includes generating, based on the nominal position and a subset of the system property data corresponding to the compliance of the second robotic surgery arm, a plurality of expected positions of the second robotic surgery arm. The computer-implemented method further includes determining a search area including a subset of the image data based on the plurality of expected positions and identifying, using an object recognition technique within the search area, a second distal end of the second robotic surgery arm within the image data. Other embodiments of this aspect include corresponding computer systems, apparatus, and computer programs recorded on one or more computer storage devices, each configured to perform the actions of the methods.

In another aspect a robotic surgery system is described including one or more processors, a first robotic surgery arm, a camera positioned at a first distal end of the first robotic surgery arm, and a second robotic surgery arm, The robotic surgery system also includes one or more non-transitory computer-readable media including computer-executable instructions that, when executed by the one or more processors, cause the one or more processors to receive image data from the camera, receive system property data providing dimensions of the second robotic surgery arm, and receive kinematic pose data providing a plurality of joint angles of the second robotic surgery arm. The instructions further cause the processors to determine, based on the system property data and the kinematic pose data, a nominal position of the second robotic surgery arm within the image data. The instructions then cause the processors to determine a search area including a subset of the image data including the nominal position. The instructions further cause the processors to identify, using an object recognition technique within the search area, the second robotic surgery arm within the search area.

In yet another general aspect a computer system, including a memory having computer-executable instructions and one or more processors communicatively coupled to the memory and configured to access the memory and execute the computer-executable instructions to perform operations. The instructions cause the computer system to receive image data from a camera disposed at a first distal end of a first robotic surgery arm, receive system property data describing compliance of a second robotic surgery arm, and receive kinematic pose data describing a plurality of joint angles of the second robotic surgery arm. The instructions further cause the computer system to determine, based on the system property data and the kinematic pose data, a nominal position of the second robotic surgery arm within the image data. The instructions then cause the computer system to generate, based on the nominal position and a subset of the system property data corresponding to the compliance of the second robotic surgery arm, a plurality of expected positions of the second robotic surgery arm. The instructions further cause the computer system to determine a search area including a subset of the image data representing the second robotic surgery arm, based on the plurality of expected positions and identifies, using an object recognition technique within the search area, the second robotic surgery arm within the image data.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
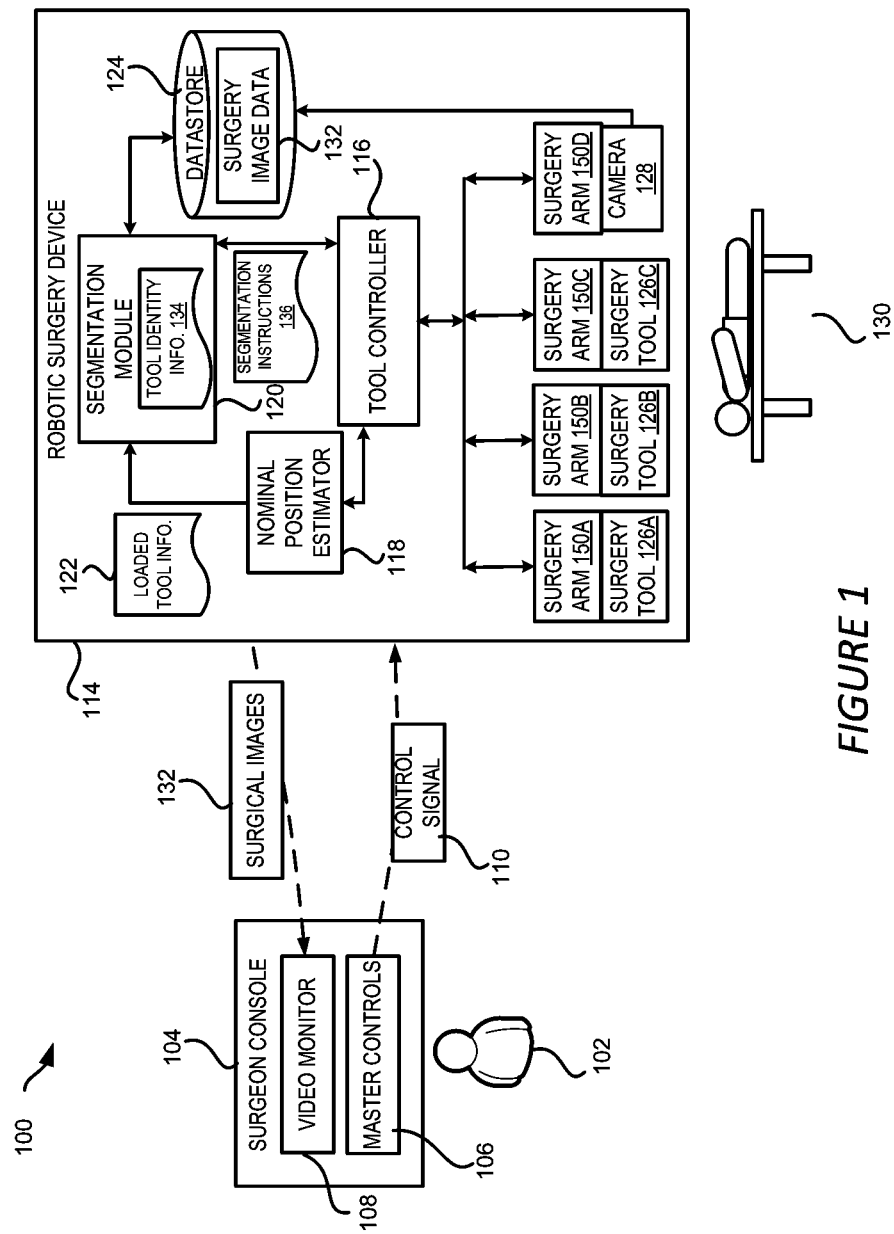
FIG. 1 shows an example of a robotic surgery system for implementing techniques relating to robot kinematics based surgical tool segmentation, according to at least one example.

Examples are described herein in the context of improving image segmentation of surgery tools in a robotic surgery system based on robot kinematics. Those of ordinary skill in the art will realize that the following description is illustrative only and is not intended to be in any way limiting. For example, techniques described herein may be applied to any field where image segmentation or object recognition techniques are used. One additional example may include in video motion capture systems using robot armatures to support image sensors, where kinematics of the robotic armatures are known and trackable. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made to achieve the developer's specific goals, such as compliance with application and business-related constraints, and that these specific goals will vary from one implementation to another and from one developer to another.

In an illustrative example, a robotic surgery system includes one or more robotic surgery arms each including one or more surgery tools. The robotic surgery system also includes a surgeon console for managing operation of the robotic surgery arms and a computer system having modules loaded thereon for performing techniques described herein that are controllable through the surgeon console. For example, the computer system includes modules for image segmentation to identify the surgery tools within images of the surgery provided at the surgeon console. A surgeon can operate these surgery tools through controls at the surgeon console. A camera is also loaded onto one of the robotic surgery arms to capture images or videos of a surgery procedure performed using the surgery tools.

During robotic surgery procedures, the limited field of view of the endoscope can limit a surgeon's ability to orient themselves with respect to the field of view and understand the orientation of the robot surgery arms and associated surgery tools based on the same field of view. Additionally, presenting three-dimensional information gathered by a stereoscopic endoscope and displayed on a two-dimensional display can add extra difficulty for surgeons to orient within the field of view. Identifying surgery tools and robot surgery arms within videos or images of surgeries can provide additional context and orientation information for a surgeon to reduce a possibility of surgeon error. Identifying surgery tools is typically accomplished through image segmentation.

Image segmentation is a process that subdivides an image into constituent parts or objects. The subdividing may be carried out to varying levels depending on the application. For example, in some instances, the image may be subdivided down to a pixel level over the entire image. Correctly identifying portions of a surgery tool in each subdivision, especially of a pixel-level subdivision is resource intensive and time consuming. In one basic example of image segmentation, each subdivision is analyzed and a decision is made as to whether the subdivision includes a portion of the object to be identified. In other cases, edges between objects may be identified first, and subsequently a desired object may be identified based on the edges of items identified in the image. Other segmentation methods and processes are known to those with skill in the art and intended to be encompassed by this description.

The robotic surgery system, or a computer system within the robotic surgery system, maintains a kinematic model of the robotic arm holding the surgery tool and a kinematic model of the robotic arm holding the camera. The robotic surgery system uses these two models to estimate a nominal position of the surgery tool relative to the camera. The robotic surgery system uses this position to narrow a search area within the field of view of the camera on which to perform image segmentation and identify surgery tools. The reduction in the search area enabled by determining the position of the surgery tool relative to the camera conserves computing resources and increases segmentation speed because less of the image data must be searched and processed by a segmentation module to identify objects and object edges. By limiting the amount of data that must be fed through the module, the module is able to search the images while only performing a fraction of the processing. For example, in some present instances a segmentation module may analyze each pixel of an image frame to identify particular objects within the image, by limiting to a portion of the image frame, fewer pixels are analyzed thereby increasing the speed of object recognition through segmentation.

Surgical tools and instruments are identified and monitored in surgery videos using image segmentation methods according to this disclosure. Present segmentation of objects in video frames of robotic surgery to identify surgical tools and instruments within a field of view is slow and computationally resource-intensive and require searching and performing image segmentation algorithms across entire video frames. The technology presented herein increases the speed and efficiency of surgery tool segmentation for identifying surgical tools associated with a robotic surgery system by narrowing a search area within image data captured by the camera based on kinematic robot data describing the nominal position of the surgery tool and the camera. The technologies described herein reduce computational burden and resources used to identify surgery tools within surgery image data and thereby increase the speed of processing image data through image segmentation to identify surgery tools. Because the surgery image data is restricted or limited based on the kinematics of the robotic arms, object detection and segmentation techniques can be performed on a smaller region of the image data to identify the surgery tools.

This illustrative example is given to introduce the reader to the general subject matter discussed herein and the disclosure is not limited to this example. The following sections describe various additional non-limiting and non-exhaustive examples and examples of increasing the speed and efficiency of surgery tool segmentation based on robot kinematics.

Referring now to FIG. 1, FIG. 1 shows an example robotic surgery system 100 for implementing techniques relating to robot kinematics based surgical tool segmentation, according to at least one example. The robotic surgery system 100 includes a robotic surgery device 114 configured to operate on a patient 130. The robotic surgery system 100 also includes a surgeon console 104 connected to the robotic surgery device 114 and configured to be operated by a surgeon 102 to control and monitor the surgeries performed by the robotic surgery device 114. The robotic surgery system 100 might include additional stations (not shown in FIG. 1) that can be used by other personnel in the operating room, for example, to view surgery information, video, etc., sent from the robotic surgery device 114. The robotic surgery device 114, the surgeon console 104 and other stations can be connected directly or through a network, such as a local-area network ("LAN"), a wide-area network ("WAN"), the Internet, or any other networking topology known in the art that connects the robotic surgery device 114, the surgeon console 104 and other stations.

The robotic surgery device 114 can be any suitable robotic system that can be used to perform surgery procedures on a patient 130. For example, the robotic surgery device 114 may have one or more robotic surgery arms 150 connected to a base. The robotic surgery arms 150 may be manipulated by a tool controller 116, which may include one or more user interface devices, such as joysticks, knobs, handles, or other rotatable or translatable devices to effect movement of one or more of the robotic surgery arms 150. The robotic surgery arms 150 may be equipped with one or more surgery tools 126 to perform aspects of a surgery procedure. For example, the robotic surgery arms 150A-150C may be equipped with surgery tools 126A-126C, (which may be referred to herein individually as a robotic surgery arm 150 or collectively as the robotic surgery arms 150 and a surgery tool 126 or collectively as the surgery tools 126). The surgery tools 126 can include, but are not limited to, tools for grasping for holding or retracting objects, such as forceps, graspers and retractors, tools for suturing and cutting, such as needle drivers, scalpels and scissors, and other tools that can be used during a surgery. Each of the surgery tools 126 can be controlled by the surgeon 102 through the surgeon console 104 and the tool controller 116.

In addition, the robotic surgery device 114 may be equipped with one or more cameras 128, such as an endoscope camera, configured to provide a view of the operating site to guide the surgeon 102 during the surgery. In some examples, the camera 128 can be attached to a robotic surgery arm 150D of the robotic surgery device 114 controlled by the tool controller 116 as shown in FIG. 1. In other examples, the camera 128 can be attached to a mechanical structure of the robotic surgery device 114 that is separate from the robotic surgery arms 150.

Different robotic surgery devices 114 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgery robots, including those without robotic surgery arms 150, such as for endoscopy procedures, may be employed according to different examples. It should be understood that while only one robotic surgery device 114 is depicted, any suitable number of robotic surgery devices 114 may be employed within a robotic surgery system 100.

In some examples, robotic surgery devices 114 (or a respective controller) may be configured to record data during a surgery procedure. For example, images and videos of the surgery procedures performed by the robotic surgery device 114 can also be recorded and stored for further use. For instance, a datastore 124 can be employed by the robotic surgery device 114 to store surgery image data 132 of surgery procedures captured by the camera 128. The surgery image data 132 can be stored as separate images or as one or more video files.

In the example shown in FIG. 1, surgery image data 132 of a robotic surgery procedure captured by the camera 128 can also be transmitted to the surgeon console 104 and be displayed on a video monitor 108 in real time so that the surgeon 102 can view the procedure while the surgery tools 126 are being operated on the patient 130. In this example, the surgeon 102 can use the surgeon console 104 to control the surgery tools 126 and the camera 128. The surgeon 102 can use controls 106 on the surgeon console 104 to maneuver the surgery tools 126 and camera 128 by sending control signals 110 to the corresponding surgery tools 126 or camera 128. For example, the surgeon 102 can move the camera 128 to various positions with respect to the patient body to find the proper operating site. The surgeon 102 can then move the camera 128 to a position where a surgery tool 126 to be actively used is located to bring the surgery tool 126 inside the field of view of the camera 128. The surgeon 102 may then move the surgery tool 126 along with the camera 128 to the operating site.

Methods and implementation of a nominal position of a surgery tool 126 in the field of view of the camera 128 can be determined by determining the position of the surgery tool 126 relative to the camera 128 based on the kinematics of the robotic surgery arms 150. The robotic surgery device 114 can include a nominal position estimator module 118 to estimate the nominal position of the surgery tool 126 based on the relative positioning of the camera 128 and the surgery tool 126 as determined based on the robotic arm kinematics. The prediction can be performed through a kinematic chain model of the robotic arm 150 of the robotic surgery device 114 holding the surgery tool 126 and a kinematic chain model of the robotic arm 150D holding the camera 128. The kinematic chain model can estimate the nominal position of the surgery tool 126 based on the dimensions and connectivity of the links and joints of the robotic arm 150. Information collected from various sensors deployed in the robotic arm 150, such as the direction and degree of a rotation at a joint, can also be used to perform the estimation. The compliance of the segments and joints of the robotic arm 150 may also be modelled and considered in the estimation. In addition, computer aided design (CAD) models of the surgery tool can also be used to estimate the nominal position of the surgery tool 126.

A segmentation module 120 is stored on a memory device of the robotic surgery device 114 which includes instructions and processes for a processor to perform image segmentation and/or object recognition techniques on the surgery image data 132 captured by the camera 128. Segmentation instructions 136 include standard segmentation techniques and/or object recognition techniques, such as trained convolutional neural networks, thresholding, clustering, edge detection, generalized fast marching method, Viola-Jones object detection frameworks, and scale-invariant feature transforms.

The segmentation module 120 interacts with the other elements of the robotic surgery system 114 to determine a nominal position of the surgery tools 126 within the surgery image data 132 at the datastore 124 and based on the nominal position select a subset of the surgery image data 132 as a search area in which to perform object recognition techniques to identify the actual position of the surgery tools 126 within the surgery image data 132. The segmentation module 120 estimates the nominal position based on kinematic pose data describing the configuration of the surgery arms 150 from the datastore 124 and the tool controller. Once the segmentation module 120 identifies the nominal position, it determines a search area representing a subset of the surgery image data 132 based on the nominal position. The segmentation module 120 then performs object recognition within the search area. By performing object recognition on only the determined search area, the system is able to more quickly and efficiently identify the surgical tool within the image.

The segmentation module 120 resolves the problem described above in a number of ways including accounting for compliance of the joints in determining a search area, generating a probability map of possible locations based on the compliance data (described with respect to FIG. 8 below), adjusting the nominal position based on previous identifications of surgery tools 126. In this way, the segmentation module 120 is able to limit and reduce the portion of the surgery image data 132 that must be searched by an object recognition technique to identify the surgery tools 126 because compliance and deflection errors can be accounted for in determining a nominal position and subsequent search area.

It should be understood that although FIG. 1 illustrates the various modules, such as the segmentation module 120, the nominal position estimator module 118, the tool controller 116 and the datastore 124, are included in the robotic surgery device 114, one or more of these modules can be implemented in different ways within a robotic surgery system. For example, the functionality described above need not be separated into discrete modules, or some or all of such functionality may be located on a computing device separate from the robotic surgery device 114, such as a central controlling device connected to the robotic surgery device 114 directly or through a network and configured to control the operations of the robotic surgery system 100.

Figure 2:
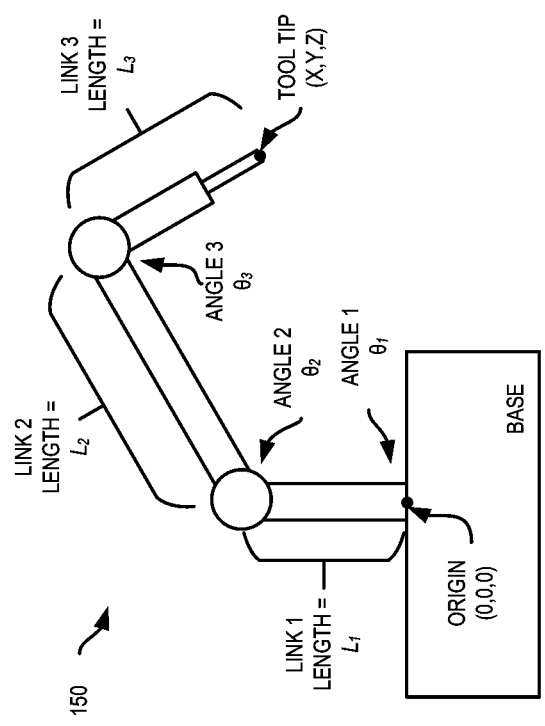
FIG. 2 shows an example kinematic chain model of a robotic arm holding a surgery tool that can be used by techniques to estimate the position of the surgery tool, according to at least one example.

FIG. 2 shows an example kinematic chain model of a robotic arm holding a surgery tool that can be used by techniques to estimate the nominal position of the surgery tool, according to at least one example. In this example, the robotic surgery arm 150 includes three links, Link 1, Link 2 and Link 3, having respective lengths L1, L2 and L3. The three links are connected by two joints having respective angles $\theta_2$ and $\theta_3$. The base of the robotic arm and Link 1 form angle $\theta_1$. If the base of the robotic arm is used as the origin (0,0,0), the coordinates (X,Y,Z) of the nominal position of the tool tip in the three-dimensional space can be determined based on the length of each of the three links, namely, L1, L2 and L3 and the values of angles $\theta_1$, $\theta_2$ and $\theta_3$. Similarly, the nominal position of the camera 128 can be predicted by using the kinematic chain model of the robotic arm holding the camera 128. The values of the angles and the length of the links are all included in kinematic pose data, though in some examples, the kinematic pose data used to calculate the position of the surgery tools 126 includes only the values of the angles described above, with the lengths defined as constants in a separate system property dataset.

Once the nominal positions of the robotic surgery arms 150 including the surgery tools 126 and the camera 128 are determined, the relative position of each surgery tool 126 with regard to the camera 128 can also be determined based on the kinematic pose data. The nominal positions of the robotic surgery arms 150 includes the specific combination of the orientations of the joints and linkages of the robotic surgery arms 150 including pose information describing the entire orientation of the robotic surgery arms 150. The relative position of the camera 128 and the surgery tools 126 is determined using the nominal positions of each robotic surgery arm 150 in a three-dimensional coordinate system. Each robotic surgery arm 150 uses a coordinate system for locating the end with the surgery tool 126 and therefore, the three-dimensional relative position can be geometrically determined based on the coordinate systems once the nominal positions are known.

However, various errors, such as compliance errors and measurement errors, can cause the nominal position of the surgery tools 126 and/or the camera 128 to be inaccurate. This problem may be especially prominent when the robotic surgery device 114 has long, compliant robotic surgery arms 150 with multiple joints. For example, in such cases, small deflections or errors in proximal joint measurements can become relatively large errors in nominal position for the surgery tool 126 or the camera 128. As a result, a surgery tool 126 that is expected to be at a first location inside the field of view of the camera 128 might be actually at a second location within the field of view of the camera 128 or even outside the field of view of the camera 128.

Figure 3:
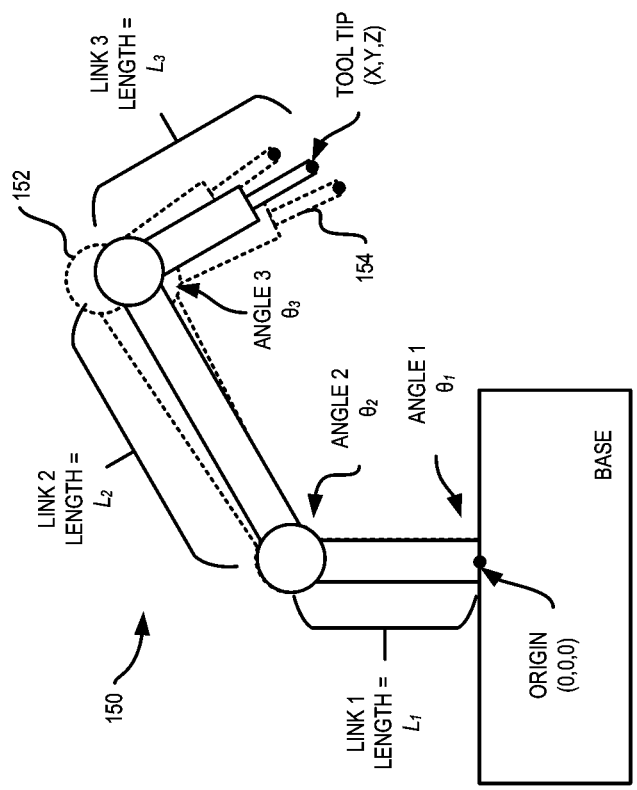
FIG. 3 shows the robotic arm of FIG. 2 with outlines displaying representations of possible positions of the robotic arm linkages based on joint compliance, according to at least one example.

FIG. 3 shows the robotic arm of FIG. 2 with outlines displaying representations of possible positions of the robotic arm linkages based on joint compliance, according to at least one example. Compliance refers to a stiffness of the robot surgery arm 150. For example, each of the joints of the robot surgery arm will have some degree of flexibility or compliance. The stiffness of each joint of the robot surgery arms 150 allows the end of the robot surgery arms 150 to be in multiple different locations based on a single set of joint positions. In other words, compliant actuators and joints in robot surgery arms 150 allow deviations, of varying degrees based on the level of compliance, from an expected position due to external applied forces.

A first outline 152 represents one possible position of the robotic arm 150. The first outline 152 shows a possible maximum position of the robotic surgery arm 150 based on the compliance at the joints with angles 2 and 3. Angle 2 may be at a certain angle $\theta_2$ with compliance that describes a range of deviation from $\theta_2$. Perturbation of the robotic surgery arm 150 in a first direction is shown by the first outline 152, and in a second direction is shown by a second outline 154. As depicted, the tool tip is expected or estimated to be at a location (X,Y,Z), but may in fact be anywhere between the tool tips of the first outline 152 and the second outline 154. A more complex kinematic model of a robotic surgery arm 150 requires accounting for compliance at each joint and along the length of each segment of the robotic arm to generate the total possible range of positions of the tool tip in space. A feed forward simulation may generate the full possible range of tool tip locations based on the compliance data and link lengths, which are known either based on system property data describing permanent features of the robotic surgery arm 150 such as link lengths as well as kinematic data describing joint angles and compliance. In some examples, the system property data also includes predetermined or default compliance data, such as a default compliance range of one-half of a degree in each degree of freedom for a joint.

Figure 4:
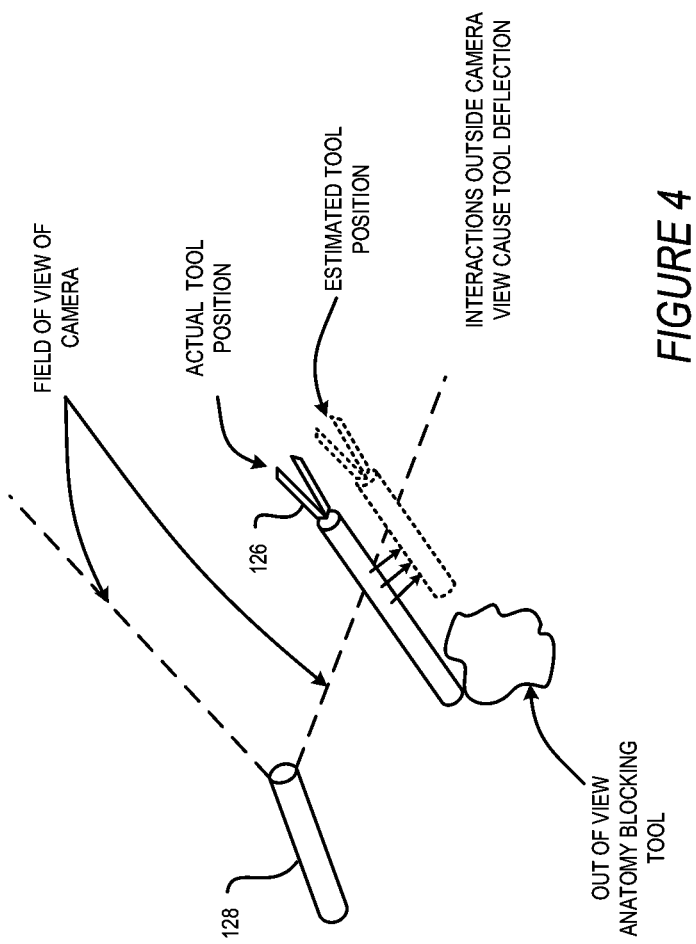
FIG. 4 shows an example of a representation of a difference in nominal versus actual position in a robotic surgery system for implementing in image segmentation techniques using robot kinematics, according to at least one example.

FIG. 4 shows an example of a representation of a difference in nominal versus actual position in a robotic surgery system for implementation in image segmentation techniques using robot kinematics, according to at least one example. In this example, the deviation is a result of anatomy outside the field of view of the camera resisting movement of the robotic surgery arm 150 within the range of compliance of the robotic surgery arm 150. Force applied on the patient 130 by the surgery tool 126 or robotic surgery arm 150 can cause deflection on the surgery tool 126 thereby resulting in the actual position of the surgery tool 126 to be different from the expected position. In FIG. 4, the force applied by the surgery tool 126 on the out-of-view anatomy deflects the surgery tool 126 causing its position to deviate from the nominal position.

To increase the speed of tool identification and segmentation in robotic surgery video, the robotic surgery device 114 can further include a segmentation module 120 according to the technologies disclosed herein. The segmentation module 120 can analyze the surgery image data 132 captured during the surgery procedure to identify the actual position of the surgery tools represented in the surgery image data 132 and accelerate the analysis by restricting a search region within the surgery image data 132 based on kinematics of the robotic arms 150 identifying a nominal position as described above.

As used herein, the surgery image data 132 can include one or more videos of the surgery procedure captured by the camera 128 or any individual images contained in such videos. The analysis can include identifying surgery tools 126 used in the surgery procedure from the surgery image data 132, for example, through object recognition or other image/video processing techniques. The types of the identified surgery tools 134 and their status, such as open or closed can also be determined, in combination with additional instrument logging data describing information such as energy being applied to the surgery tools 134.

Figure 5:
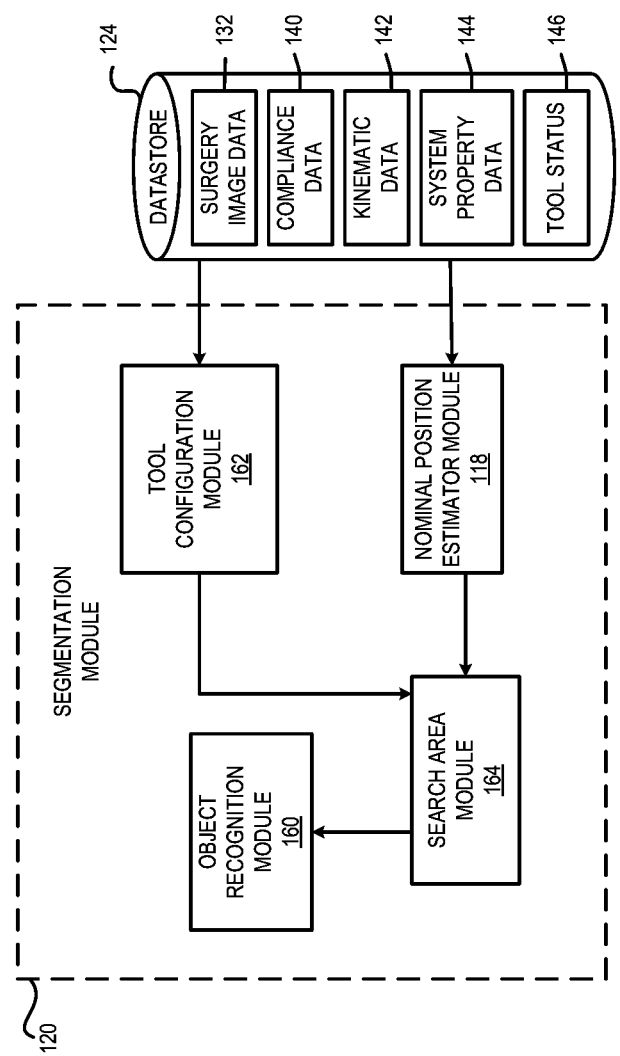
FIG. 5 shows a block diagram illustrating aspects of the segmentation module for implementing techniques of image segmentation using robot kinematics, according to at least one example.

Referring now to FIG. 5, FIG. 5 shows a block diagram illustrating aspects of the segmentation module for implementing techniques of image segmentation using robot kinematics, according to at least one example. As illustrated in FIG. 5, the segmentation module 120 can include a nominal position estimator module 118 to estimate or predict an expected position of the surgery tool 126 within the field of view of the camera 128. The nominal position estimator module 118 receives data from the datastore 124 including system property data 144 and kinematic data 142. The system property data 144 includes data describing the robotic surgery system 100 such as the length of linkages of the robotic arms 150. The kinematic data 142 describes the angles and positioning of the robotic arms 150 as described with respect to FIG. 2 above. The nominal position estimator module 118 further receives surgery image data 132 from an endoscope collecting image data of a surgery procedure connected to an end of the robotic surgery arm 150D.

A tool configuration module 162 receives tool status data 146 from the datastore 124 or the robotic surgery system 100. The tool configuration module 162 may communicate with a search area module 164 to selectively perform operations of the segmentation module 120 when the tool status data 146 indicates that a surgery tool 126, such as a grasper, is closed or in a compact configuration. When surgery tools 126 are in a compact configuration, such as when a grasper is closed, the amount of area of the surgery image data 132 covered by the surgery tool 126 is smaller than when the surgery tools are opened or otherwise expanded. The search area module 164 receives data from the nominal position estimator module 118 and the tool configuration module 162 to select a limited portion of the surgery image data 132 on which to perform object recognition to identify surgery tools 126. The detection of the surgery tools 126 can be performed by using object recognition by the object recognition module 160 or by other image/video processing techniques.

For example, a trained machine-learning ("ML") technique, such as a convolutional neural network, can be trained and used to recognize surgery tools 126 from surgery image data 132. Although convolutional neural networks are described herein, any suitable ML technique may be trained to recognize different surgery tools 126 from surgery image data 132, such as a long short-term memory ("LSTM") technique, a dynamic time warping ("DTW") technique, a hidden Markov model ("HMM"), etc., or combinations of one or more of such techniques—e.g., CNN-LSTM, CNN-HMM or MCNN (Multi-Scale Convolutional Neural Network), Mark-R-CNN (Mask Region CNN), Single Shot Detection (SSD), or You Only Look Once (YOLO) based approaches.

The convolutional neural network can be trained, or fine-tuned if the neural network is pre-trained, by using a set of training samples including surgery image data 132 and corresponding labeling indicating a location of the surgery tools 126 in the surgery image data. After the training, the convolutional neural network can estimate a location within the surgery image data 132 where the surgery tools 126 exist.

The detected surgery tools 126 can then be sent to a tool labeling module, which may include a machine-learning system or other recognition module for performing object recognition to identify the types of the identified surgery tools 126 can be recognized based on the surgery image data 132 containing the detected surgery tools 126. The tool types can include, but are not limited to, tools for grasping for holding or retracting objects, such as forceps, graspers and retractors, tools for suturing and cutting, such as needle drivers, scalpels and scissors, and other tools that can be used during a surgery. Depending on the surgery being performed or to be performed, sub-type of the surgery tools can also be identified. For example, the tool labeling module can identify a grasper tool as a fenestrated grasper for grasping delicate tissue like peritoneum and bowel, or a traumatic grasper for securing thicker tissue or organs.

It should be appreciated that the methods presented above for detecting the surgery tools 126 and identifying the tool location within the surgery image data 132 are for illustration only and should not be construed as limiting. Other methods can also be employed to facilitate the detection of the surgery tools 126 and the tool type. For instance, information obtained through imaging mechanisms other than the camera 128 can also be used to facilitate the identification of the surgery tools 126. These imaging mechanisms can include, but are not limited to, the ultrasound imaging, optical contrast imaging, fluorescent imaging and so on. The nominal position output by the nominal position estimation module 118 and the tool configuration output by the tool configuration module 162 can be sent to the search area module 164 to determine or select a restricted section of the surgery image data 132 in which to instruct the object recognition module 160 to perform object recognition to identify the surgery tools 126.

Figure 6:
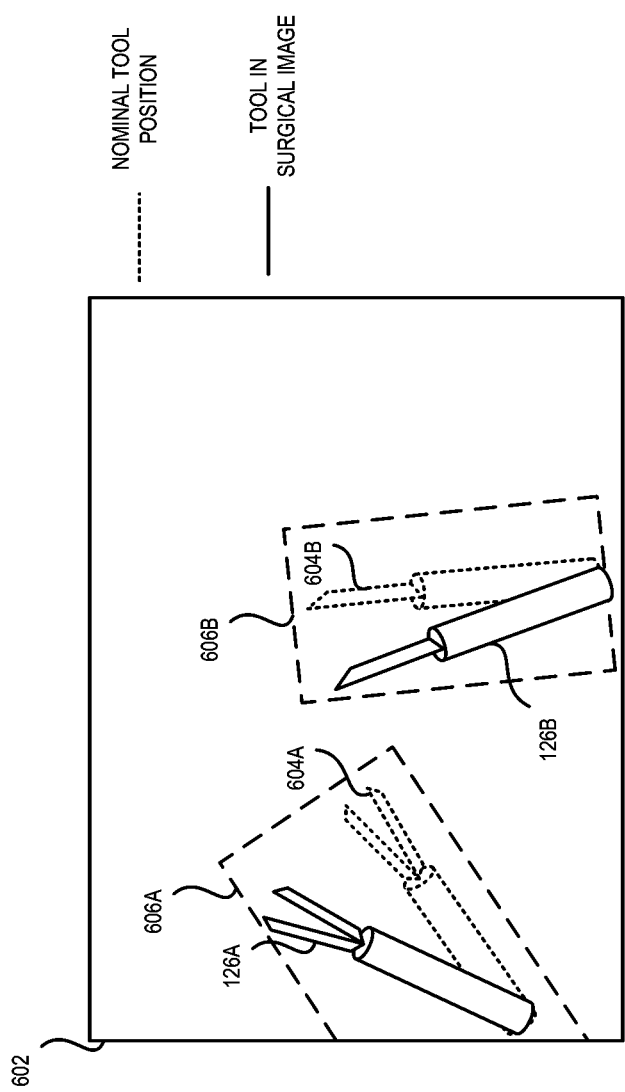
FIG. 6 shows an example video frame captured by an endoscope of a robotic surgery system depicting representations of nominal and actual locations of surgery tools and representations of search boxes containing both for implementation in image segmentation techniques using robot kinematics, according to at least one example.
Figure 7:
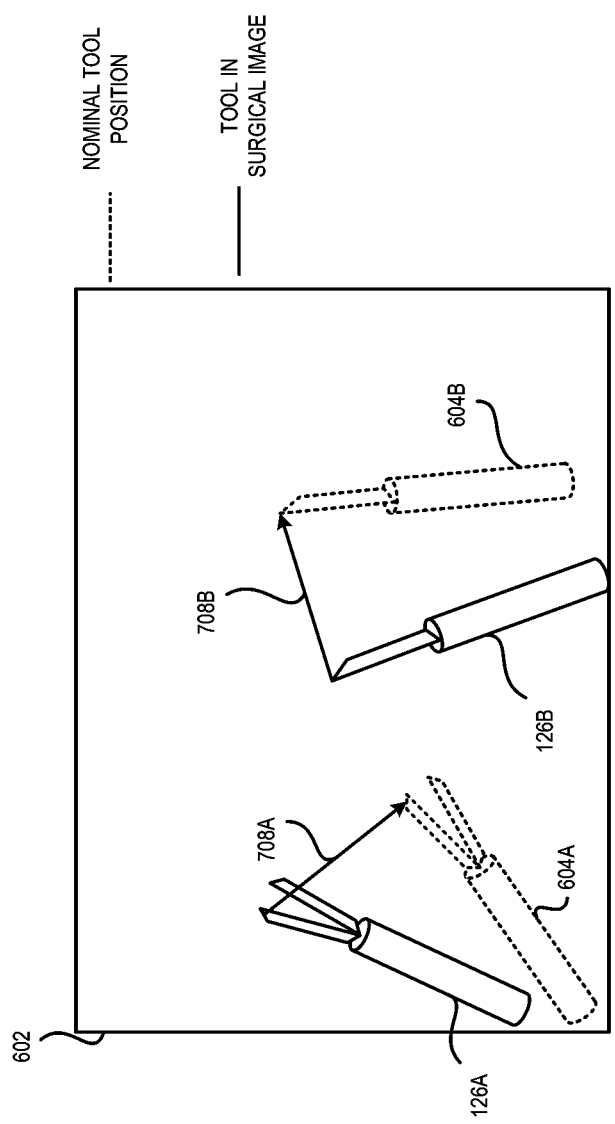
FIG. 7 shows an example video frame captured by an endoscope of a robotic surgery system depicting a representation of an offset vector between a nominal and actual surgery tool position for implementation in image segmentation techniques using robot kinematics, according to at least one example.
Figure 8:
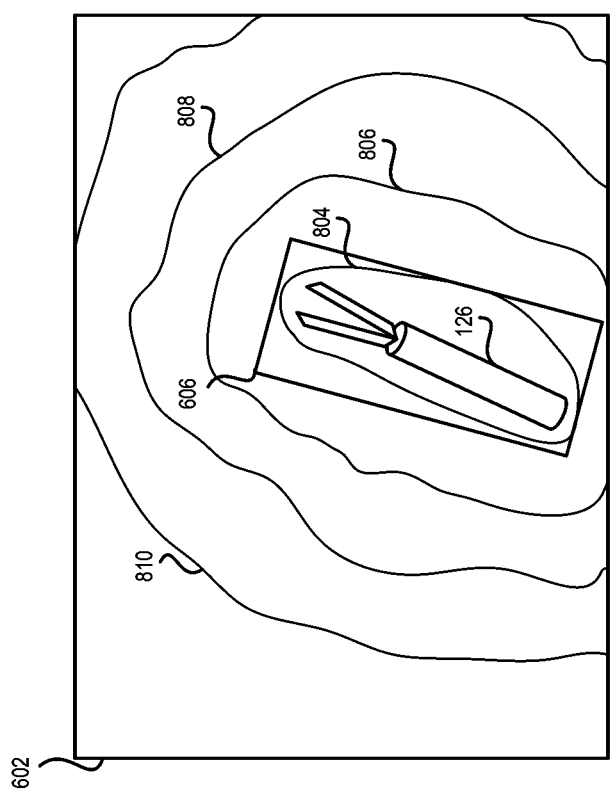
FIG. 8 shows a representation of a probability map of possible locations of a surgery tool and a search area positioned based on the probability map for implementation in image segmentation techniques using robot kinematics, according to at least one example.

FIGS. 6 through 8 depict example video frames captured by an endoscope of a robotic surgery system depicting representations of techniques implemented by the segmentation module 120, according to at least some examples. The illustrations shown in FIGS. 6 through 8 may be used in coordination or combination with one another to select the search area 606 within the surgery image data 132. FIG. 6 depicts a display 602 on which surgery image data 132 as received from a camera 128 is displayed. To generate a target search area, the tool kinematic data are converted from the three-dimensional space and projected to the two-dimensional image plane, based on the characteristics of the endoscope and its setup, such as the distance between image sensors of a stereo endoscope. The segmentation module 120 described herein determines a nominal position 604 of the surgery tools 126 in relation to the camera 128 and the field of view of the camera 128. When the search area module 164 receives the nominal position 604 of the surgery tools 126, the search area module identifies a limited search area 606 of the field of the display 602 on which to perform object recognition. For example, a first nominal position 604A of the surgery tool 126A is identified within the surgery image data 132 based on the kinematic data 142 and also compliance data 140 as described herein. A first search area 606A is a subset of the surgery image data 132 and is selected and sized based on the first nominal position 604A as well as data relating to the surgery tool such as the size of the surgery tool 126. The first search area 606A represents a significantly smaller subsection of surgery image data 132 for processing by an object recognition module 160. This results in a significantly reduction in the use of computer resources and faster object recognition. In the case of two or more surgery tools 126, additional search areas 606B can be identified based on additional nominal positions 604B for additional surgery tools 126B.

In some examples, such as shown in FIG. 7, the nominal position 604 may differ from an actual position of the surgery tool 126. In a first set of image data, a difference vector 708 is identified describing a spatial difference between the nominal position 604 and the image data of the surgery tool 126. The difference vector 708 represents a vector describing the location difference between the coordinate position (X1,Y1,Z1) of the nominal position 604 and the location (X2, Y2, Z2) of the surgery tool 126 within the surgery image data 132. This difference vector 708 may be the result of out of view anatomy blocking or restricting motion of the robotic surgery arm 150. In other examples, the difference described by the difference vector 708 may be a result of the compliance of the robotic surgery arm 150.

The difference vector 708 may be used in coordination with the search area 606 described in FIG. 7. For example, the nominal position estimator module 118 may estimate the nominal position 604 but may also take into account previous difference vectors 708 to locate a position of the search area 606. This is because the difference described by the difference vector 708 may, in some instances, be consistent between sets of surgery image data 132 on which the segmentation module 120 acts.

FIG. 8 depicts a representation of a probability map of possible locations of a surgery tool 126 and a search area positioned based on the probability map for implementation in image segmentation techniques by the segmentation module 120, according to at least one example. FIG. 8 depicts an illustration of a probability map identifying possible or expected positions of the surgery tool 126. The nominal position estimator module 118 may use the kinematic data 142 and the compliance data 140 to generate the probability map. For example, using a feed-forward simulation, the kinematic chain described in FIG. 2 can be used to generate a number of possible locations for the surgery tool 126. Because of compliance of the robotic arms 150, and potentially due to out-of-view anatomy, the position of the surgery tool 126 may not match with the nominal position 604. The feed forward simulation begins at the first joint or base of the robotic surgery arm 150 with the position of the joint as defined by the kinematic data 142. The compliance of that joint may be used to generate a range of possible positions for the robotic surgery arm 150. As the feed forward simulation proceeds, the second joint of the robotic surgery arm 150 is then simulated based on position and compliance to further simulate the position of the robotic surgery arm 150. The feed forward simulation proceeds until the end of the robotic surgery arm 150 including the surgery tool 126 is simulated.

Based on the possible positions of the robotic surgery arm 150, the probability map shown in FIG. 8 can be generated. For example, positions within the simulation with a higher probability of having the surgery tool 126 are identified by boundaries or contours 804, 806, 808, and 810. In some instances, the pixels within contour 804 will be of a color, such as green, indicating a high probability, while pixels outside of contour 810 will be of a different color such as black indicating a lower probability, with pixels in the regions defined by contours 806 and 808 a gradient between the two. The search area 606 may then be sized and located within the surgery image data 132. For instance, the search area 606 may be sized and located based on a highest probability region 804 of the probability map, in the example of the green pixels described above, the search area 606 may be selected to encompass all of the bright green pixels indicating a high probability. In other instances, a threshold may be selected, the threshold representing a percentage or probability above which the search area module 164 may have confidence that the surgery tool 126 is within the threshold. The probability map may be regenerated after movement of the robotic surgery arm 150, either partially or in whole. For example, regenerating just the final link or distal end of the feed forward simulation of the robotic surgery arm 150 may conserve computer resources.

Figure 9:
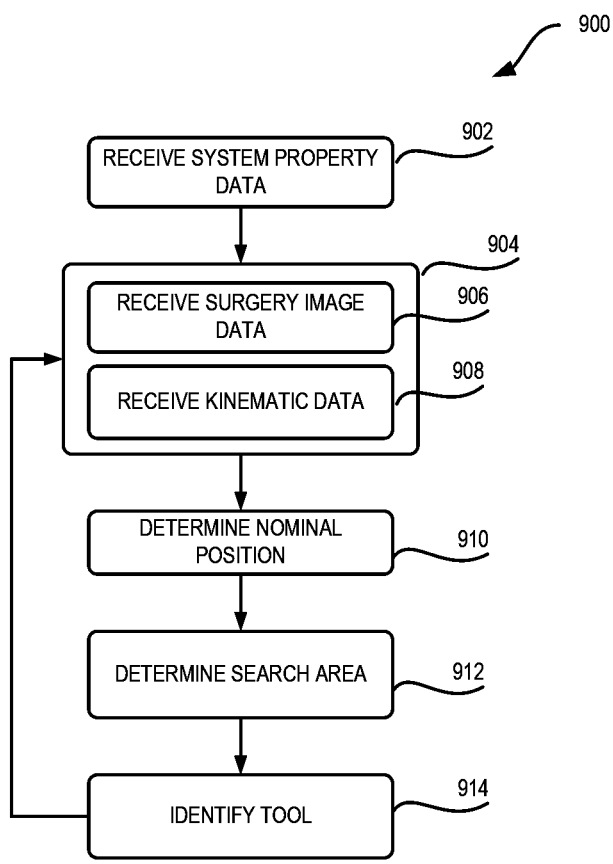
FIG. 9 shows an example method for improving surgery tool segmentation using robot kinematics, according to at least one example.
Figure 10:
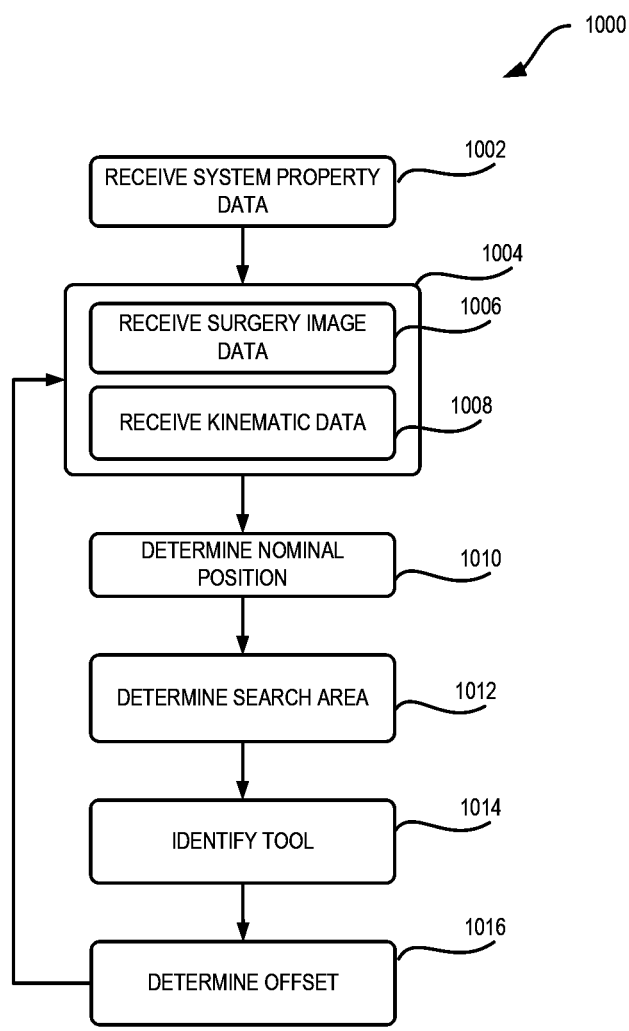
FIG. 10 shows an example method for improving surgery tool segmentation using robot kinematics, according to at least one example.
Figure 11:
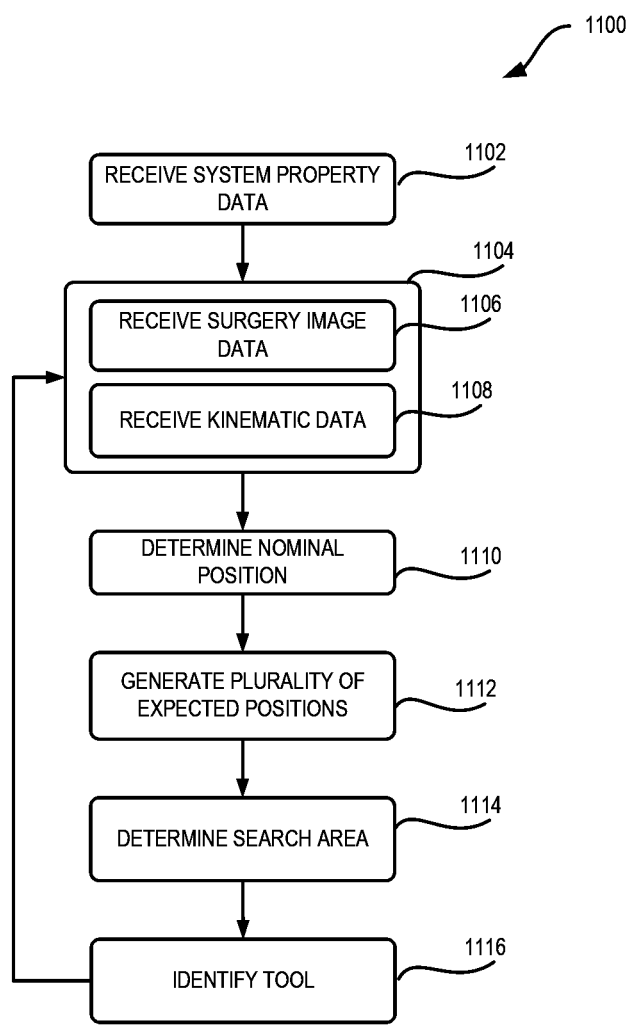
FIG. 11 shows an example method for improving surgery tool segmentation using robot kinematics, according to at least one example.

FIGS. 9-11 illustrate example methods for improving surgery tool segmentation using robot kinematics, according to at least a few examples. FIGS. 9-11 illustrate flow diagrams showing processes 900, 1000, and 1100, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Referring now to FIG. 9, FIG. 9 shows an example process 900 for identifying surgery tools 126 within surgery image data 132. The process 900 is performed by the segmentation module 120 executing in a computing device, such as a computing device described in FIG. 12. The computing device may be included in the surgeon console 104. In some examples, process 900 and any other process described herein may be performed, at least in part, by a human operator.

In process 900, at block 902, the segmentation module 120 receives system property data 144. The system property data 144 in this example describes characteristics of the robotic surgery device 114. For example, the system property data 144 may include the length of links of the robotic arms 150 and compliance data 140 as described herein. Additionally, the system property data 144 describes other fixed properties of the robotic surgery system 100 including the location of the robotic arms 150 in reference to the patient 130 and the dimensions of the robotic surgery system 100. In other examples, the system property data may include additional or different combinations of such information.

At block 904, active surgery data, which is data received by the robotic surgery system 100 during a surgery procedure—such as data from the camera 128, the robotic arms 150, and various sensors—is received by the computing device from the robotic surgery device 114. In particular, the segmentation module 120 on the computing device receives surgery image data 132 from the camera 128 at sub-block 906 and receives the kinematic data 142 at sub-block 908. The kinematic data 142 may be received by accessing a datastore such as the datastore 124 or from one or more sensors on the robotic surgery device 114 that measure kinematic characteristics of the robotic surgery device 114. The surgery image data 132 includes videos and still images of data captured by an endoscope. The kinematic data 142 describes the position of the joints of the robotic arms 150.

At block 910, the segmentation module 120 determines a nominal position of the surgery tool 126 in relation to the camera 128. The segmentation module 120 determines the nominal position based on the kinematic data 142 and the system property data 144. The segmentation module 120 may determine the nominal position based on a feed-forward simulation, taking into account the length of linkages and angle of joints of the robotic surgery arm 150 supporting the surgery tool 126 as well as the length of linkages and angle of joints of the robotic surgery arm 150D. The feed-forward simulation includes trigonometric projections based on the origin of the robotic surgery arm 150 as well as the link length and joint angles of the robotic surgery arm 150 to determine the nominal position. The segmentation module 120 may determine the nominal position of the surgery tool 126 or an end effector of the robotic arm 150 relative to the camera 128. As described above, the segmentation module 120 may determine the nominal position based on the compliance data, a probability map, a simulation of possible locations, or any other factors described herein.

At block 912, the segmentation module 120 determines a search area 606 within the surgery image data 132 based on the nominal position. The search area 606 describes a bounding box within the surgery image data 132 containing the nominal position. The search area 606 is sized based on the size of the surgery tool 126. For example, the search area may be sized to three to ten times the width of the surgery tool 126 and one to three times the length of the surgery tool 126.

The segmentation module 120 locates the search area 606 or further refines the size of the search area 606 based on additional data, such as a difference vector 708 or a probability map as described above with respect to FIGS. 7 and 8. For instance, the segmentation module 120 identifies an initial search area 606 based on the nominal position. However, to further refine the search area 606 into a smaller area, the segmentation module 120 uses difference vector 708 from a previous identification of the surgery tool 126 in the image data to offset the location of the search area 606 based on historical data. With a further refined search area 606 location, the search area 606 may be reduced in size, thereby further reducing computing resources needed for object detection.

The segmentation module 120 may locate or refine the search area 606 based on the probability map described above with respect to FIG. 8. In particular, the segmentation module 120 generates a probability map of locations for the surgery tool 126 based on the feed-forward simulation of the robotic surgery arm 150, with a higher probability in locations where the surgery tool 126 is more likely to be located. The surgery tool 126 is more likely to be located in positions where the joints are each nearest to the center of the location predicted based on the kinematic data 142. Additionally, the segmentation module 120 may use previous surgery tool identifications from previous image data or difference vectors 708 to alter the probability map. For instance, the segmentation module may adjust the probability map based on a difference vector 708. In this manner, within a single surgery or surgery device, errors within the system which result from the particular aspects of an individual robotic surgery system 114 or errors resulting from interference or force against the robotic surgery arm 150 can be adjusted for based on historical data.

Once the segmentation module 120 determines the location and size of search area 606 within the surgery image data 132, the segmentation module 120 may perform object recognition techniques or image segmentation within the search area 606 to identify the surgery tool 126 at block 914. The segmentation module 120 may use techniques known in the art for object detection, including those described above.

As shown in FIG. 9, the process 900 may be repeated for subsequent frames of surgery image data 132 by returning to block 904. The system property data 144 includes system constants for the robotic surgery device 114 and therefore does not need to be repeated in subsequent iterations of process 900. However, in instances where a linkage or system property of the robotic surgery device 114 is adjustable, such as with a telescoping linkage, the system property data 144 may be re-gathered iteratively.

FIG. 10 depicts an example process 1000 performed by one or more modules described herein for detecting surgery tools 126 using an offset from a previous surgery tool identification in image data. Blocks 1002 and 1004, including the sub-blocks 1006 and 1008, as well as block 1010 include the segmentation module 120 performing functions and processes generally as described above with respect to blocks 902, 904, 906, 908, and 910 of FIG. 9. At block 1012, the segmentation module 120 determines a search area 606 based on the nominal position as well as the difference vector 708. The segmentation module 120 determines the difference vector 708 based on a previous surgery tool 126 identified within surgery image data 132, for example at block 1016 of a previous iteration of process 1000. The previous identification and segmentation of the surgery tool 126 within the surgery image data 132 and a present iteration of process 1000 may be separated by several seconds. As such, the difference vector 708 is likely to be largely unchanged from one iteration to the next. This allows the search area 606 to be further refined, reduced in size, and more accurately placed within the surgery image data 132. In other examples, the difference vector 708 may be replaced with a previous indicator of a location of a surgery tool 126 within previous surgery image data 132 as compared to current surgery image data 132.

Following the determination and location of the search area 606, the segmentation module 120 identifies the surgery tool 126 in block 1014. This may be performed according to the same methods and processes described above, including any known object detection methods. After the segmentation module 120 identifies the surgery tool 126, the segmentation module determines a new difference vector 708 describing the difference between the nominal position and the identified surgery tool 126 within the surgery image data 132. The process 1000 then returns to block 1004 and the segmentation module 120 determines a new search area at block 1012 based on the new difference vector 708.

FIG. 11 represents a process 1100, performed by the segmentation module 120, for identifying a surgery tool 126 within surgery image data 132 during a surgery procedure similar to processes 900 and 1000 including a step for generating nominal positions of the robotic arms 150 and basing the search area determination on a probability of surgery tool positions determined based on the nominal positions. Other steps within the process 1100, including block 1102, 1104, 1106, 1108, 1110, and 1116 perform similar functions as blocks 1002, 1004, 1006, 1008, 1010, and 1014 of process 1000. At block 1112, the segmentation module 120 generates a plurality of expected positions of the surgery tool 126 based on the kinematic data 142, compliance data 140, and system property data 144 as described above. The plurality of expected positions, in some examples, forms an envelope of all possible surgery tool locations or may be used to generate a probability map as described above with respect to FIG. 8. The segmentation module 120 determines the location and size of the search area in block 1114 based on the plurality of nominal positions from block 1112.

In any of the processes described above, the process may be performed selectively based on a tool configuration. The segmentation module 120 receives tool status data 146 which describes a configuration of a surgery tool 126, such as an open or closed configuration for a grasper. When the grasper is closed, the profile of the surgery tool is smaller than when the grasper is opened. Therefore, selectively performing processes 900, 1000, or 1100 when the tool is closed allows the search area 606 to be as small as possible and therefore further conserve computing resources and speed up the segmentation and surgery tool detection process.

Figure 12:
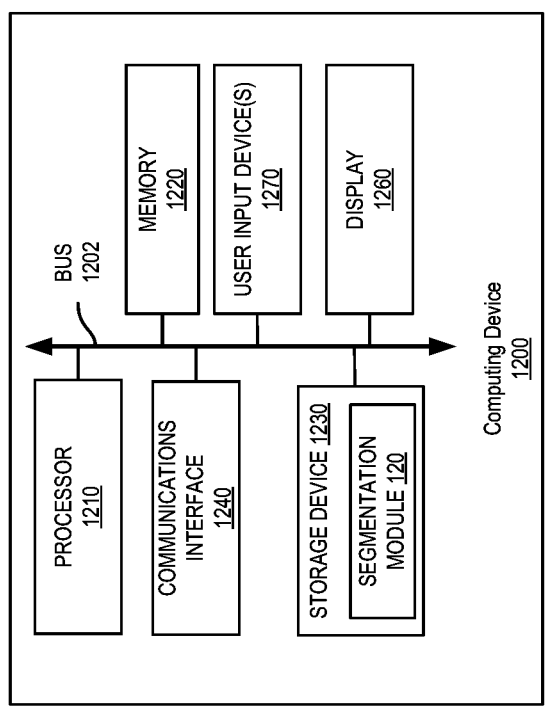
FIG. 12 shows an example computing device suitable for implementing aspects of the techniques and technologies presented herein, according to at least one example.

Referring now to FIG. 12, FIG. 12 shows an example computing device 1200 suitable for use in example systems or methods for improving robotic surgery safety through video processing. The example computing device 1200 includes a processor 1210 which is in communication with the memory 1220 and other components of the computing device 1200 using one or more communications buses 1202. The processor 1210 is configured to execute processor-executable instructions stored in the memory 1220 to perform security check of the robotic surgery device 114 according to different examples, such as part or all of the example processes 900, 1000, and 1100 described above with respect to FIGS. 9, 10, and 11. The computing device, in this example, also includes one or more user input devices 1270, such as a keyboard, mouse, touchscreen, microphone, etc., to accept user input. The computing device 1200 also includes a display 1260 to provide visual output to a user.

The computing device 1200 can include or be connected to one or more storage devices 1230 that provides non-volatile storage for the computing device 1200. The storage devices 1230 can store system or application programs and data used by the computing device 1200, such as modules implementing the functionalities provided by the segmentation module 120. The storage devices 1230 might also store other programs and data not specifically identified herein.

The computing device 1200 also includes a communications interface 1240. In some examples, the communications interface 1240 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions using terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A computer-implemented method, comprising:
    receiving image data from a camera disposed at a first distal end of a first robotic surgery arm, the image data at least representing a second distal end of a second robotic surgery arm;
    receiving system property data providing dimensions of the second robotic surgery arm;
    receiving kinematic pose data providing a plurality of joint angles of the second robotic surgery arm;
    determining, based at least in part on the kinematic pose data and the system property data, a nominal position of the second robotic surgery arm relative to a position of the camera;
    generating a probability map of possible locations for the second robotic surgery arm based on one or more simulations of the second robotic surgery arm;
    determining a search area comprising a subset of the image data representing the second robotic surgery arm, the search area based on the nominal position and the probability map; and
    identifying, using an object recognition technique and based on a segment of the subset of the image data, the second distal end of the second robotic surgery arm within the image data.

2. The computer-implemented method of claim 1, wherein determining the nominal position of the second robotic surgery arm comprises determining a position of an end-effector disposed at the second distal end of the second robotic surgery arm relative to the position of the camera.

3. The computer-implemented method of claim 1, wherein determining the nominal position of the second robotic surgery arm is further based on compliance data comprising stiffness parameters of the second robotic surgery arm.

4. The computer-implemented method of claim 3, wherein determining the nominal position of the second robotic surgery arm comprises determining an envelope of possible locations for the second robotic surgery arm based on simulating perturbations of the second robotic surgery arm based on the compliance data, and wherein determining the search area is further based on the envelope of possible locations.

5. The computer-implemented method of claim 3, wherein the one or more simulations of the second robotic surgery arm include simulated perturbations of the second robotic surgery arm based on the compliance data.

6. The computer-implemented method of claim 5, wherein determining the search area based on the probability map comprises selecting the search area based on a predetermined confidence threshold representing a minimum probability threshold of the probability map.

7. The computer-implemented method of claim 1, further comprising:
    determining an offset value representing a three-dimensional vector describing a positional difference between the nominal position and the second robotic surgery arm based on a previous nominal position of the second robotic surgery arm and a previous identification of the second robotic surgery arm within the image data; and
    narrowing the search area based on the offset value.

8. A robotic surgery system comprising:
    one or more processors;
    a first robotic surgery arm;
    a camera positioned at a first distal end of the first robotic surgery arm;
    a second robotic surgery arm; and
    one or more non-transitory computer-readable media comprising computer-executable instructions that, when executed by the one or more processors, cause the one or more processors to:
        receive image data from the camera;
        receive system property data providing dimensions of the second robotic surgery arm;
    receive kinematic pose data providing a plurality of joint angles of the second robotic surgery arm;
        determine, based on the system property data and the kinematic pose data, a nominal position of the second robotic surgery arm within the image data;
        generate a probability map of possible locations for the second robotic surgery arm based on one or more simulations of the second robotic surgery arm;
        determine a search area comprising a subset of the image data representing the second robotic surgery arm, the search area based on the nominal position and the probability map; and identify, using an object recognition technique within a segment of the subset of the search area, the second robotic surgery arm within the search area.

9. The robotic surgery system of claim 8, wherein determining the nominal position comprises determining a position of an end-effector at a second distal end of the second robotic surgery arm relative to a position of the camera.

10. The robotic surgery system of claim 8, wherein the one or more non-transitory computer-readable media further comprise additional computer-executable instructions that, when executed by the one or more processors, cause the one or more processors to:
receive tool status data indicating when a surgery tool of the second robotic surgery arm is in an open configuration or a closed configuration, wherein the search area is determined when the surgery tool is in the closed configuration.

11. The robotic surgery system of claim 8, wherein the object recognition technique is a machine learning algorithm.

12. The robotic surgery system of claim 8, wherein determining the nominal position of the second robotic surgery arm is further based on compliance data comprising stiffness parameters of the second robotic surgery arm.

13. The robotic surgery system of claim 12, wherein determining the nominal position of the second robotic surgery arm comprises determining an envelope of possible locations for the second robotic surgery arm based on simulating perturbations of the second robotic surgery arm based on the compliance data, and wherein determining the search area is further based on the envelope of possible locations.

14. The robotic surgery system of claim 8, wherein the one or more non-transitory computer-readable media further comprise additional computer-executable instructions that, when executed by the one or more processors, cause the one or more processors to:
determine an offset value based on previous image data, the offset value representing a three-dimensional vector describing a positional difference between the nominal position and the second robotic surgery arm, and wherein determining the search area comprises adjusting the nominal position by the offset value.

15. One or more non-transitory computer-readable media comprising computer-executable instructions that, when executed by one or more computing systems, cause the one or more computing systems to:
receive image data from a camera disposed at a first distal end of a first robotic surgery arm, the image data at least representing a second distal end of a second robotic surgery arm;
receive system property data providing dimensions of the second robotic surgery arm;
receive kinematic pose data providing a plurality of joint angles of the second robotic surgery arm;
determine, based at least in part on the kinematic pose data and the system property data, a nominal position of the second robotic surgery arm relative to a position of the camera;
generate a probability map of possible locations for the second robotic surgery arm based on one or more simulations of the second robotic surgery arm;
determine a search area comprising a subset of the image data representing the second robotic surgery arm, the search area based on the nominal position and the probability map; and
identify, using an object recognition technique and based on a segment of the subset of the image data, the second distal end of the second robotic surgery arm within the image data.

16. The one or more non-transitory computer-readable media of claim 15, wherein determining the nominal position of the second robotic surgery arm comprises determining a position of an end-effector disposed at the second distal end of the second robotic surgery arm relative to the position of the camera.

17. The one or more non-transitory computer-readable media of claim 15, wherein:
determining the nominal position of the second robotic surgery arm is further based on compliance data comprising stiffness parameters of the second robotic surgery arm; and
determining the nominal position of the second robotic surgery arm comprises determining an envelope of possible locations for the second robotic surgery arm based on simulating perturbations of the second robotic surgery arm based on the compliance data, and
wherein determining the search area is further based on the envelope of possible locations.

18. The one or more non-transitory computer-readable media of claim 15, wherein the object recognition technique is a machine learning algorithm.

19. The one or more non-transitory computer-readable media of claim 15, wherein the one or more non-transitory computer-readable media further comprise additional computer-executable instructions that, when executed by the one or more computing systems, cause the one or more computing systems to:
determine an offset value based on previous image data, the offset value representing a three-dimensional vector describing a positional difference between the nominal position and the second robotic surgery arm, and wherein determining the search area comprises adjusting the nominal position by the offset value.

20. The one or more non-transitory computer-readable media of claim 15, wherein the search area is substantially rectangular.

* * * * *